(12) United States Patent
Fickenscher et al.

(10) Patent No.: US 6,506,344 B1
(45) Date of Patent: Jan. 14, 2003

(54) MULTI-CELL ROTOR

(75) Inventors: Karl Fickenscher, Marburg (DE); Oliver Kube, Frankfurt (DE)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 09/458,041

(22) Filed: Dec. 10, 1999

(30) Foreign Application Priority Data

Dec. 11, 1998 (DE) .......................................... 198 57 215

(51) Int. Cl.⁷ .......................... G01H 9/30; B32B 27/04
(52) U.S. Cl. .......................... 422/72; 422/63; 422/64; 436/43; 436/45; 436/164; 436/165
(58) Field of Search ........................ 422/63, 64, 82–85, 422/72; 436/43, 45, 164, 165

(56) References Cited

U.S. PATENT DOCUMENTS

| | | | |
|---|---|---|---|
| 4,683,120 A | * | 7/1987 | Meserol et al. |
| 5,186,896 A | | 2/1993 | Bouchée et al. |
| 5,698,450 A | * | 12/1997 | Ringrose et al. |

FOREIGN PATENT DOCUMENTS

| | | |
|---|---|---|
| DE | 39 37 609 A1 | 11/1989 |
| EP | 0 405 162 A2 | 1/1991 |
| EP | 0 417 305 A1 | 3/1991 |
| EP | 0 608 006 A2 | 7/1994 |
| WO | WO 98/38487 | 9/1998 |

* cited by examiner

Primary Examiner—Ana Fortuna
(74) Attorney, Agent, or Firm—Finnegan, Henderson, Farabow, Garrett and Dunner, L.L.P.

(57) ABSTRACT

A multi-cell rotor for an automatic analyzer for examining biological fluids includes measurement cells of different configurations and also chambers of different geometries, in identical or different configurations, which receive different volumes of fluid, arranged on the rotor and used for preparing for measurements. The chambers can fluidly communicate with one another.

33 Claims, 12 Drawing Sheets

MULTI-CELL ROTOR

BACKGROUND OF THE INVENTION

1. Field of the Invention

The invention relates to a multi-cell rotor for an automatic analyzer for examining biological fluids such as blood, blood plasma or blood serum.

2. Description of the Related Art

German Patent Application 3,937,609 already discloses a cell rotor with individual, fully enclosed cells which are arranged in a circle and extend in a radial direction. The cells each have three chambers which are divided from one another by a dam. The cells are delimited in their radial direction by essentially parallel side walls, an upper part and a lower part. Each chamber has a pipette hole through which the biological fluid to be examined or the reagents can be added. In general, the biological fluid is introduced into the chambers arranged toward the axis of rotation, and the specific reagent and, if required, diluent is introduced into the peripheral chambers, said reagent and diluent mixing and reacting with the biological fluid as soon as the latter has passed over the dam and into the peripheral chambers by means of the action of the centrifugal forces. The optical measurement is carried out perpendicular to the rotor plane, with a fixed path length of the fluid to be analyzed.

In the known cell rotors, the number and shape of the chambers and also the measurement cells are uniform. It is not therefore possible to utilize the entire space available on the rotor for measurements. Since fewer measurement cells can be accommodated then there would be if the space were utilized to the full, the costs for each individual measurement are higher than need be. In addition, the walk-away time, that is the time during which the apparatus operates without supervision, is unnecessarily limited if the maximum number of cells cannot be found space on the apparatus.

SUMMARY OF THE INVENTION

Therefore, the object of the present invention is to develop a multi-cell rotor which, while allowing optimum utilization of the available surface area, permits the accommodation of a larger number of measurement cells on the rotor and additionally provides different chamber systems for the measurement cells, which satisfy the measurement demands by means of different types of chamber shapes and chamber volumes.

This object is embodied in the present invention as a multi-cell rotor for an automatic analyzer for examining biological fluids, in which measurement cells of different configurations and also chambers of different geometries, in identical or different configurations, are arranged on said rotor, receive different volumes of fluid, are used for preparing for measurements and can communicate with one another.

BRIEF DESCRIPTION OF THE DRAWINGS

The details of this multi-cell rotor are illustrated in the attached drawings.

DETAILED DESCRIPTION OF THE PREFERRED EMBODIMENT

Figure 1:
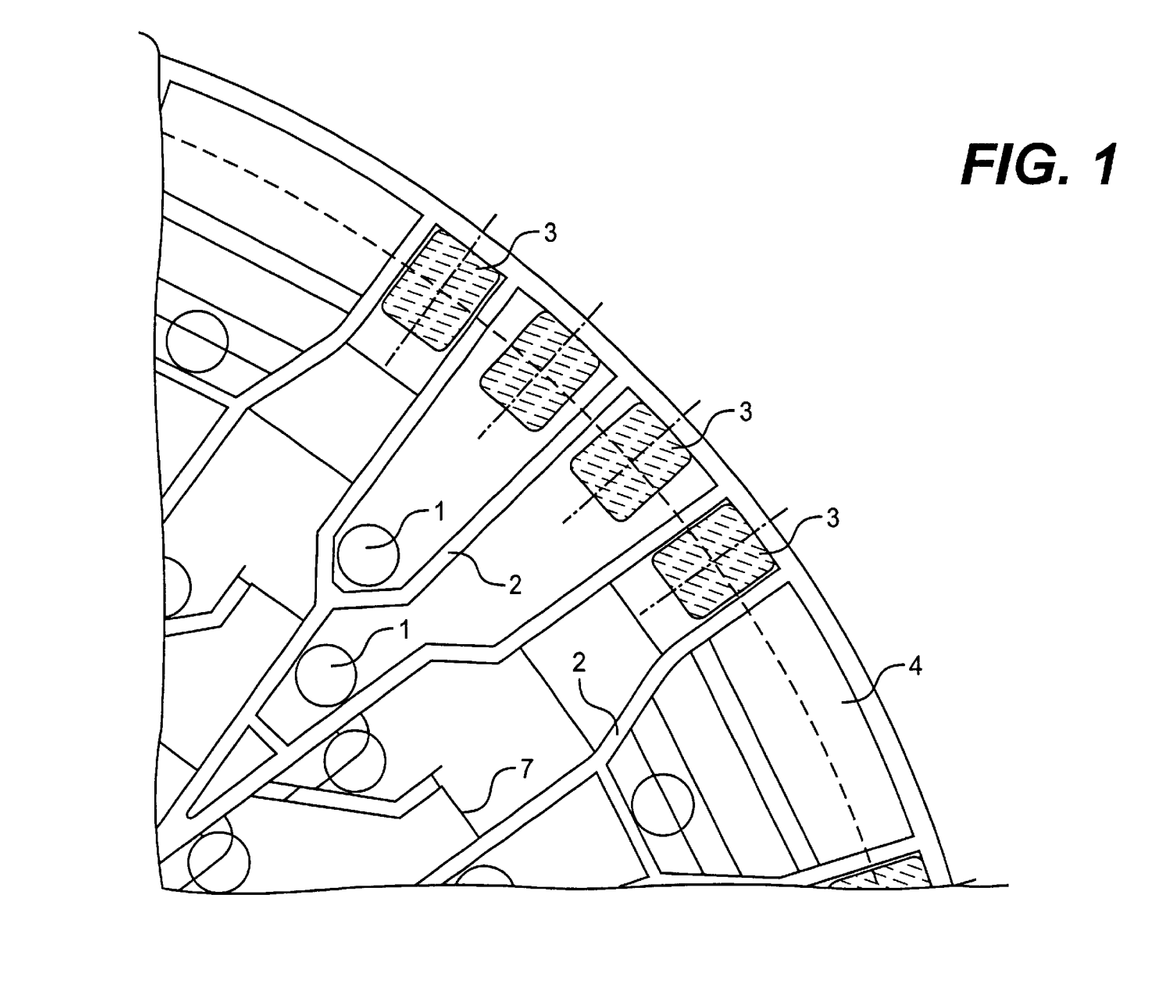
FIG. 1 is an enlarged top sectional view of a portion of the multi-cell rotor with radially arranged optical measurement windows.
Figure 2:
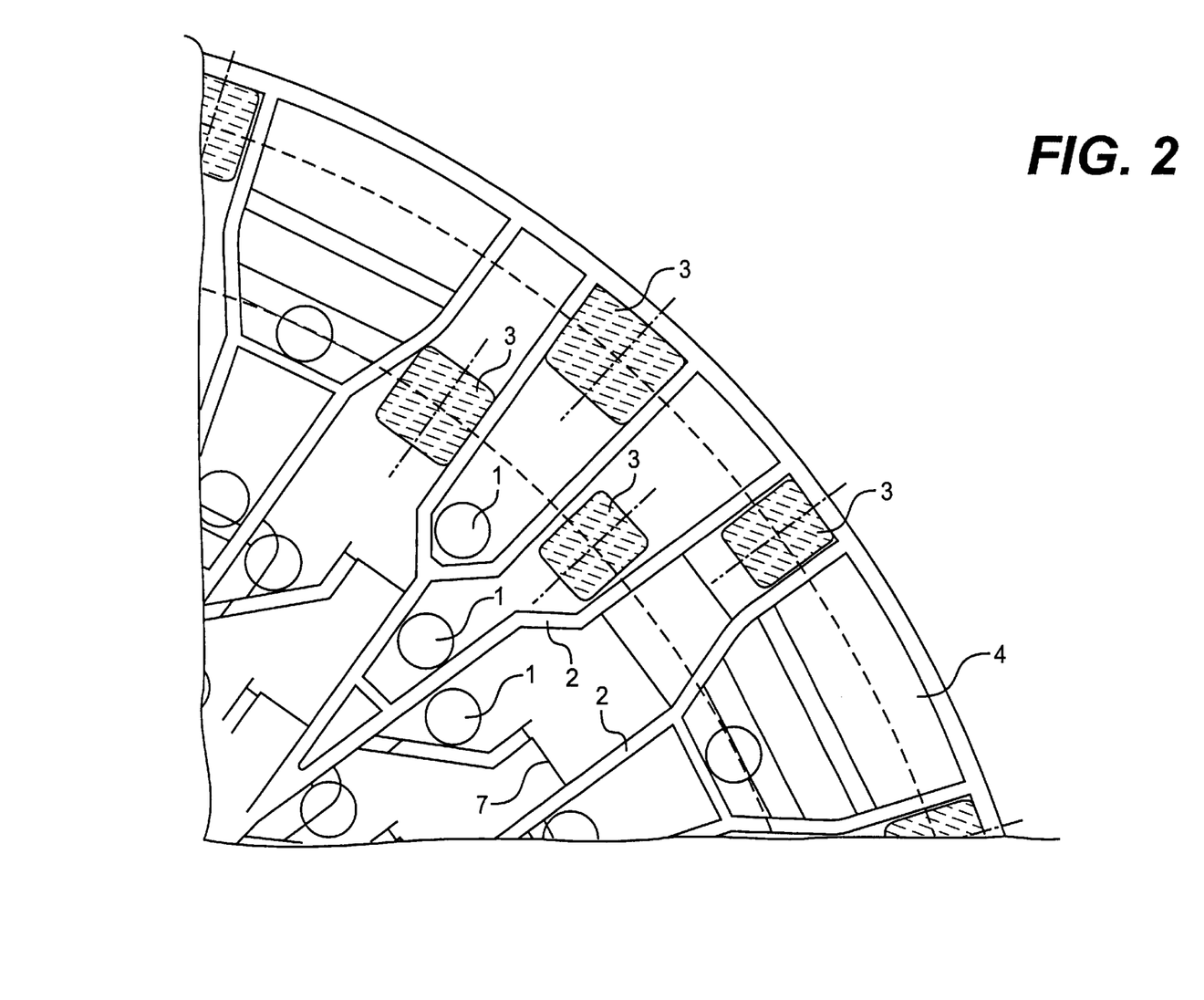
FIG. 2 is an enlarged top sectional view of a portion of a second embodiment the multi-cell rotor with differently configured measurement windows 3 which are situated at identical or different distances from one another and/or at nonuniform tangential distances from the axis of rotation of the rotor.
Figure 3:
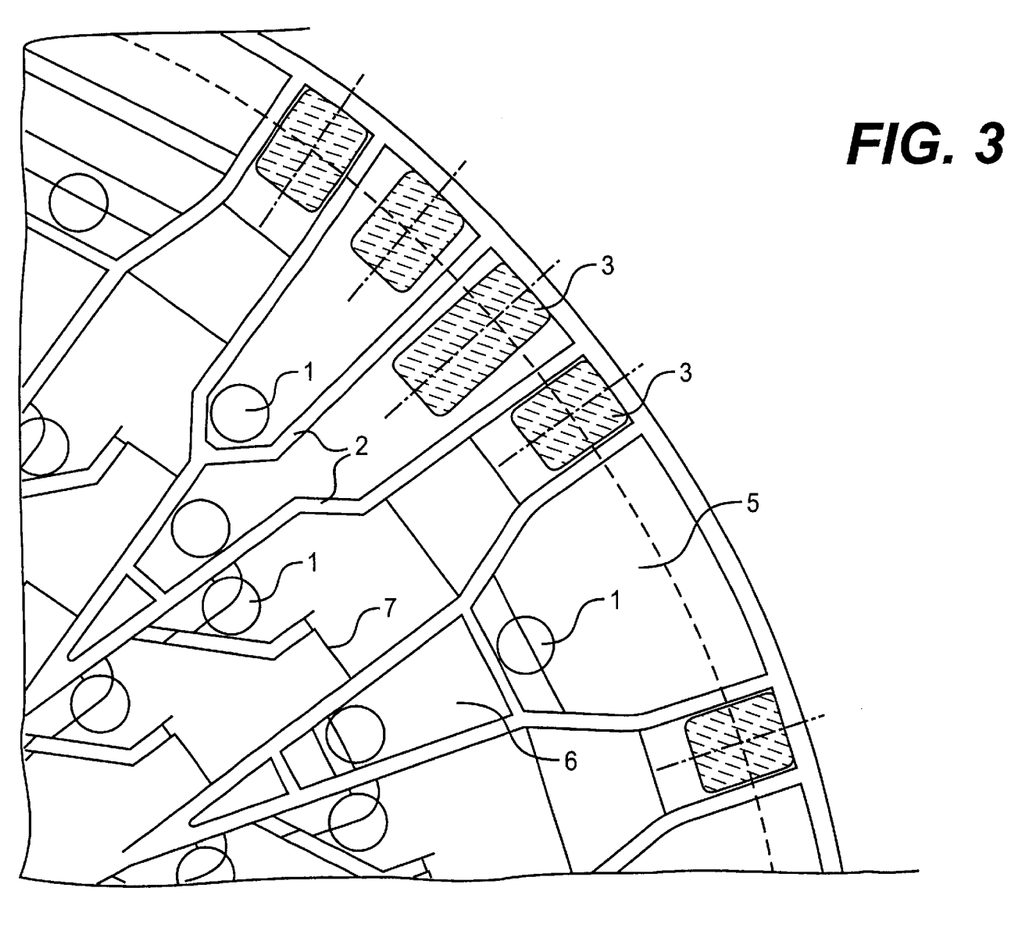
FIG. 3 is an enlarged top sectional view of an embodiment of a multi-cell rotor having measurement windows of the cells that are of identical or different sizes.
Figure 14:
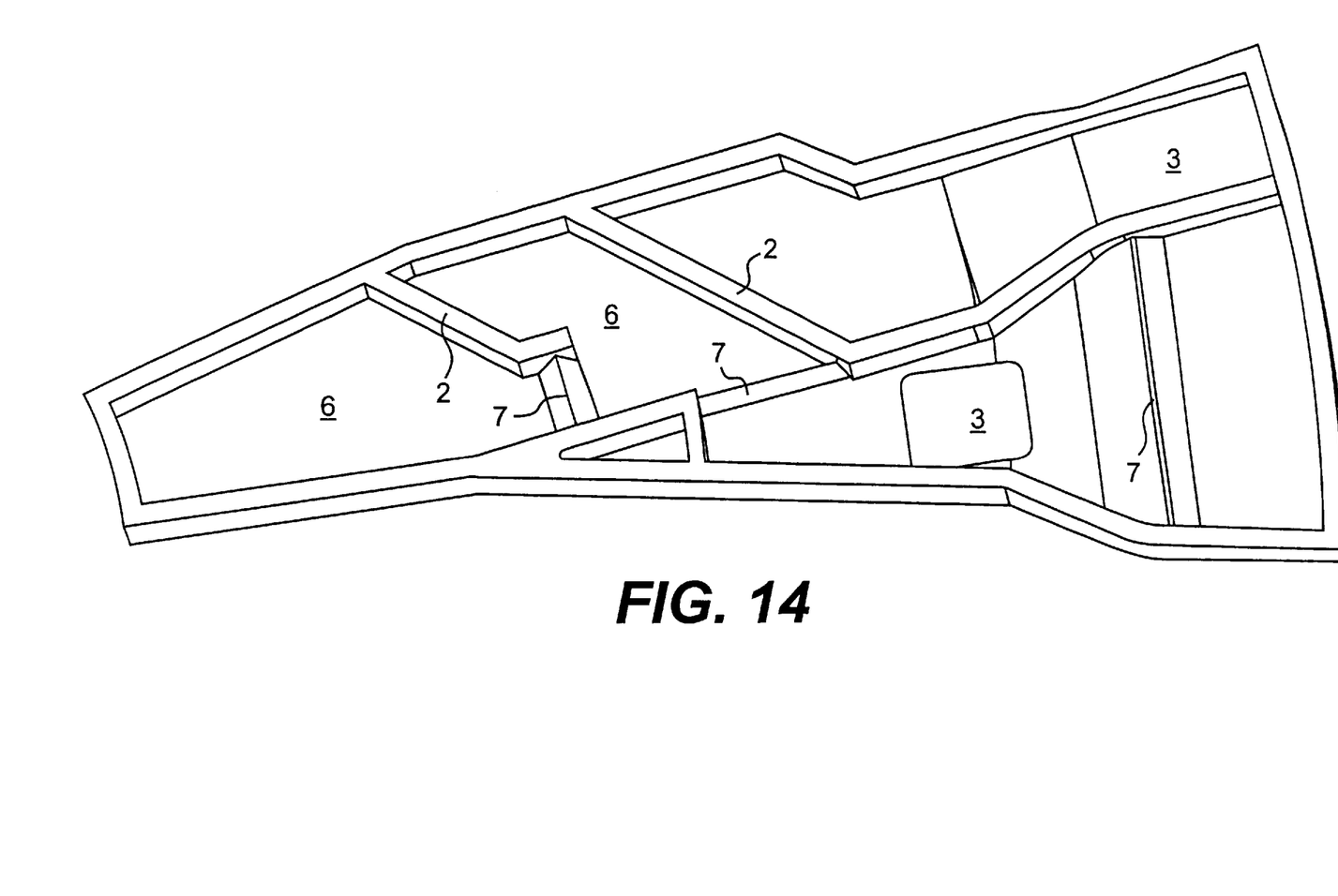
FIG. 14 is a top sectional view of a chamber system according to the present invention in which the constituents to be separated off during the analysis reaction can be transported over the ramp 7 into an outer-lying chamber so that they can no longer interfere with the measurement.
Figure 15:
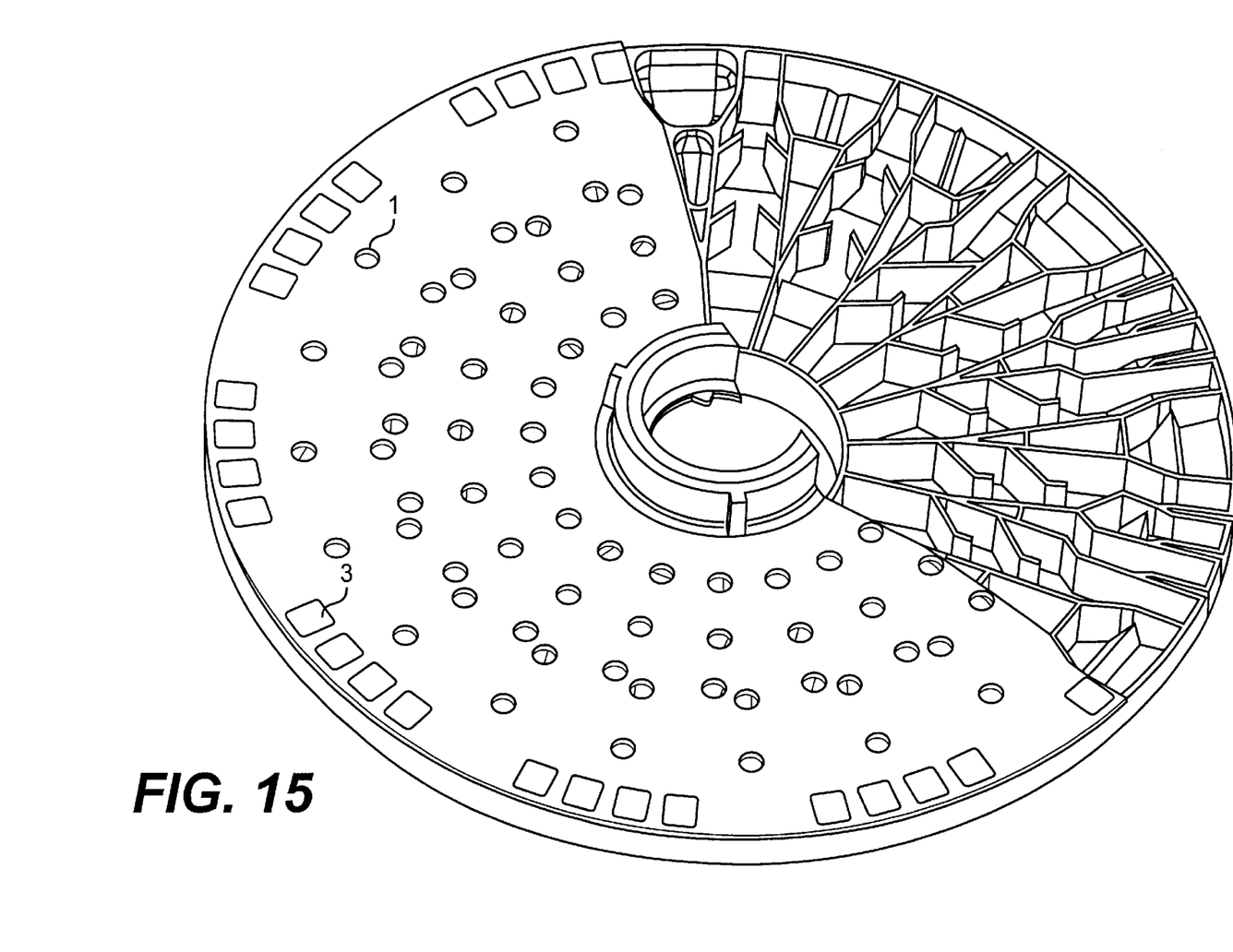
FIG. 15 is a top view including a partial sectional view of the entire surface area of a multi-cell rotor according to the present invention.

The drawings show the many possible embodiments of the multi-cell rotor according to the invention. The radial arrangement of the optical measurement windows embodied in FIG. 1 will be adequate for many measurements. In some measurements, however, optically impenetrable sediments also form which, as a result of the centrifugal force, migrate onto the inside of the outer wall of the measurement cell. In this case, a measurement in the measurement area rendered turbid by sediment is not meaningful. There is therefore a need to have the measurement window also at a certain distance from the outer edge of the measurement cell. Such an embodiment is shown in FIGS. 2, 3, and 14. As shown in FIG. 14, constituents separated off during the analysis reaction can be transported over a ramp 7 into an outer-lying chamber so that they will not interfere with the measuring process.

A particularly high degree of flexibility of the measurements can be achieved if the measurement window 3 is made very large for certain measurements, so that the viewer can freely choose in which area he wishes to optically analyze the measurement solution. This is possible in the embodiment shown in FIG. 3.

Figure 4:
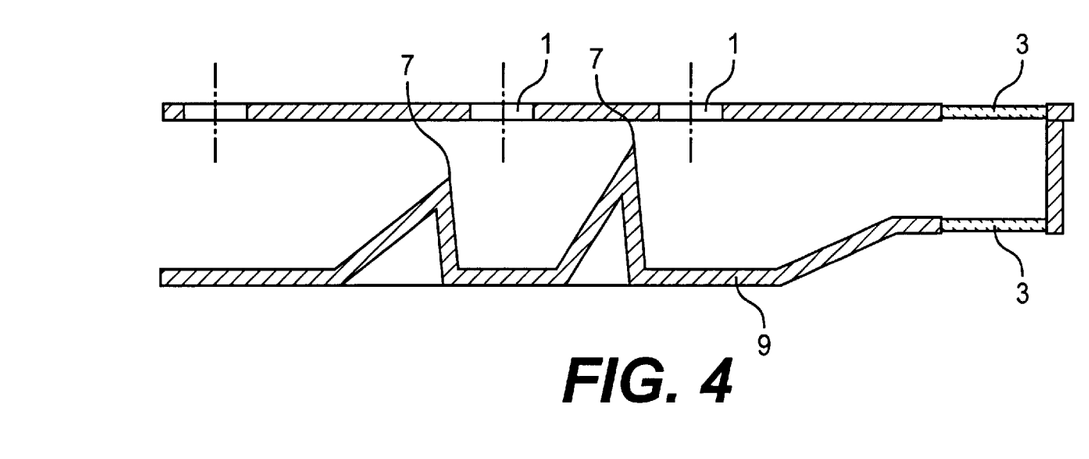
FIGS. 4 and 5 are cross-sectional views of further embodiments of measurement cells with different spacings between the measurement windows which lie opposite one another in the upper part and lower part and which can be designed as optical lenses.
Figure 5:
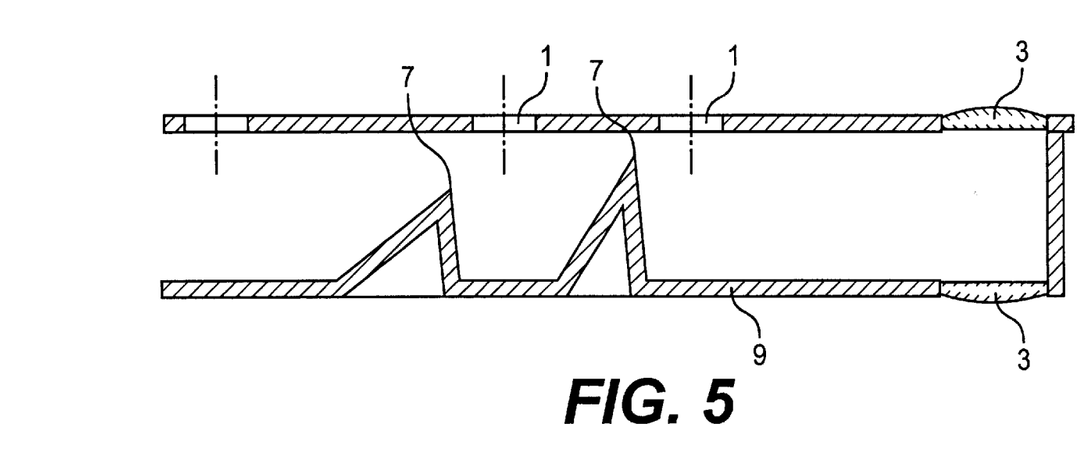

In the case of certain measurements, it is desirable not to be limited to a single path length in viewing the solution to be analyzed in the measurement cell. For this reason, FIGS. 4 and 5 show different embodiments of different configurations of the path length. Also shown are ramps 7 which divide off the entry chambers 6 filled with different reagents, but which, with sufficient rotation, permit mixing of the reagents by virtue of the fact that the fluids migrate over the ramps 7 into the more outer-lying chambers and finally into the measurement cell. The pipette holes 1 can also be clearly seen here, which permit different filling of the individual chambers and the measurement cell.

Figure 6:
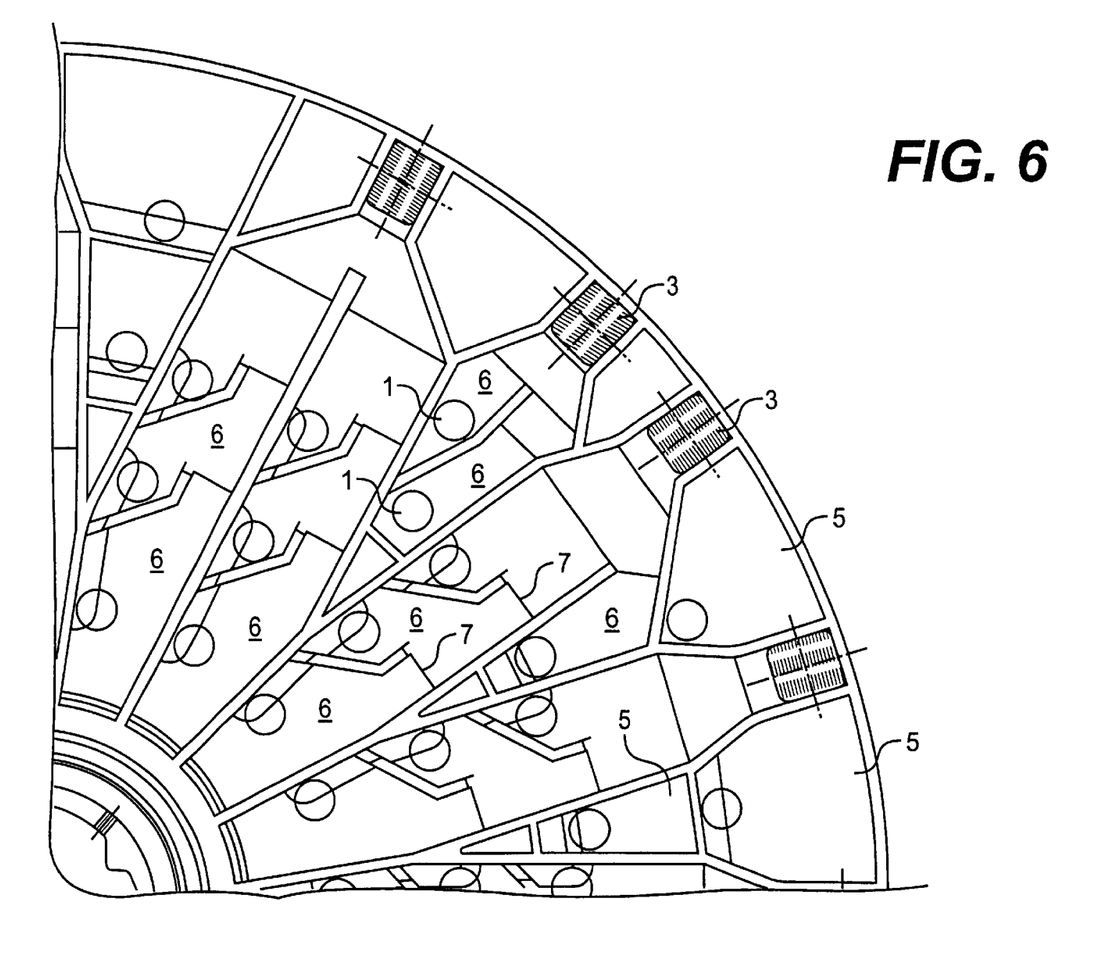
FIG. 6 is a top sectional view of a multiplicity of differently arranged entry chambers 6 which are connected to the measurement cell via ramps 7.

The multiplicity of possible chamber systems is shown by the section of the multi-cell rotor represented in FIG. 6. Each chamber here is equipped with a pipette hole 1 and is delimited from the neighboring chamber by the ramp 7. Preliminary dilution chambers 5 can also be seen. The differently arranged entry chambers 6 are connected to the measurement cell via ramps 7.

Figure 7:
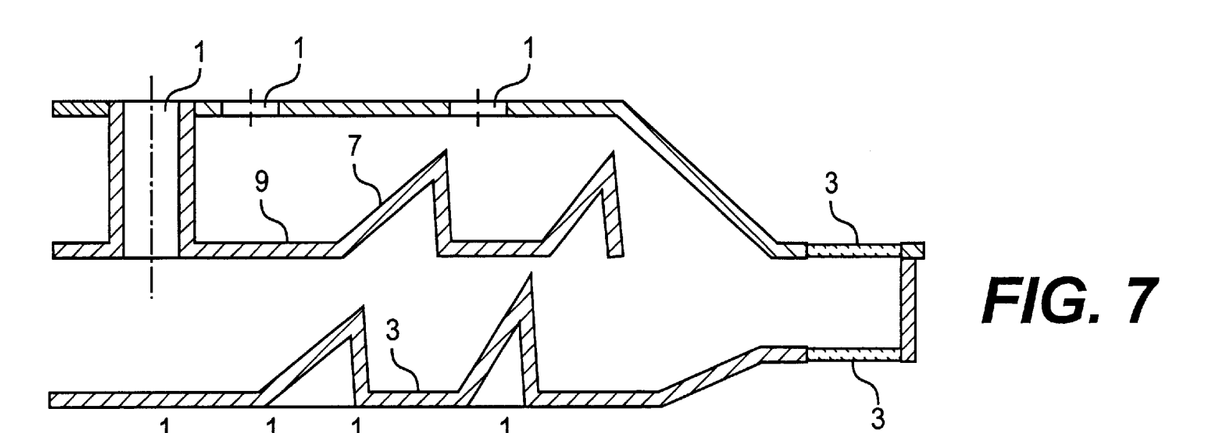
FIGS. 7 and 8 are cross-sectional views of a portion of a multi-cell rotor according to the present invention including measurement cells which are fed from a plurality of chambers or chamber combinations lying adjacent to one another or lying above one another in a plurality of layers or are fed in parallel.
Figure 8:
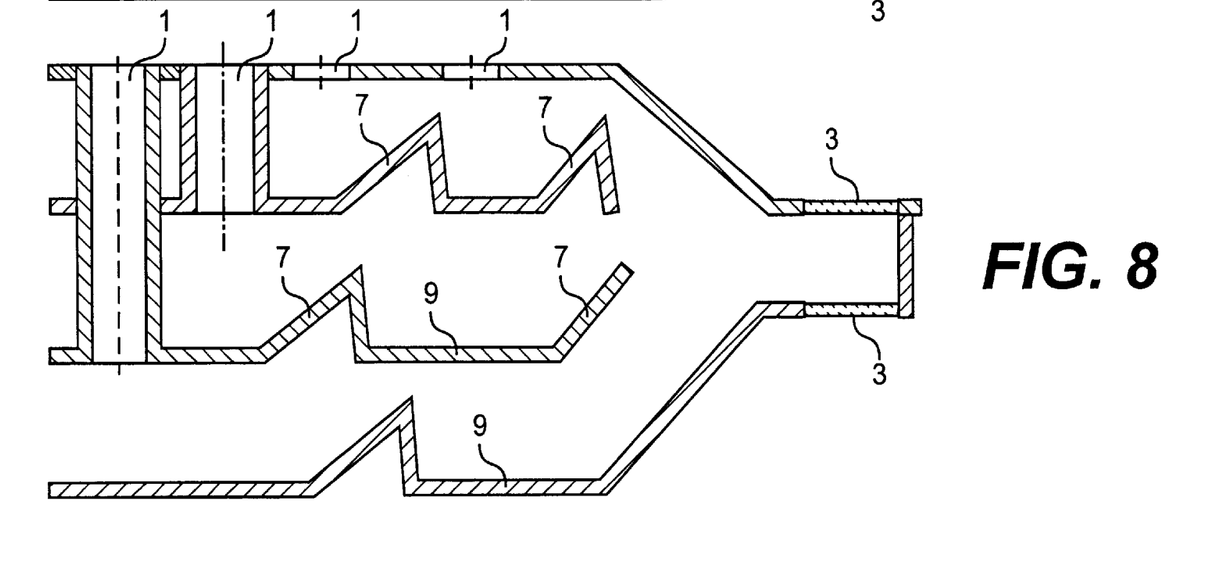
Figure 9:
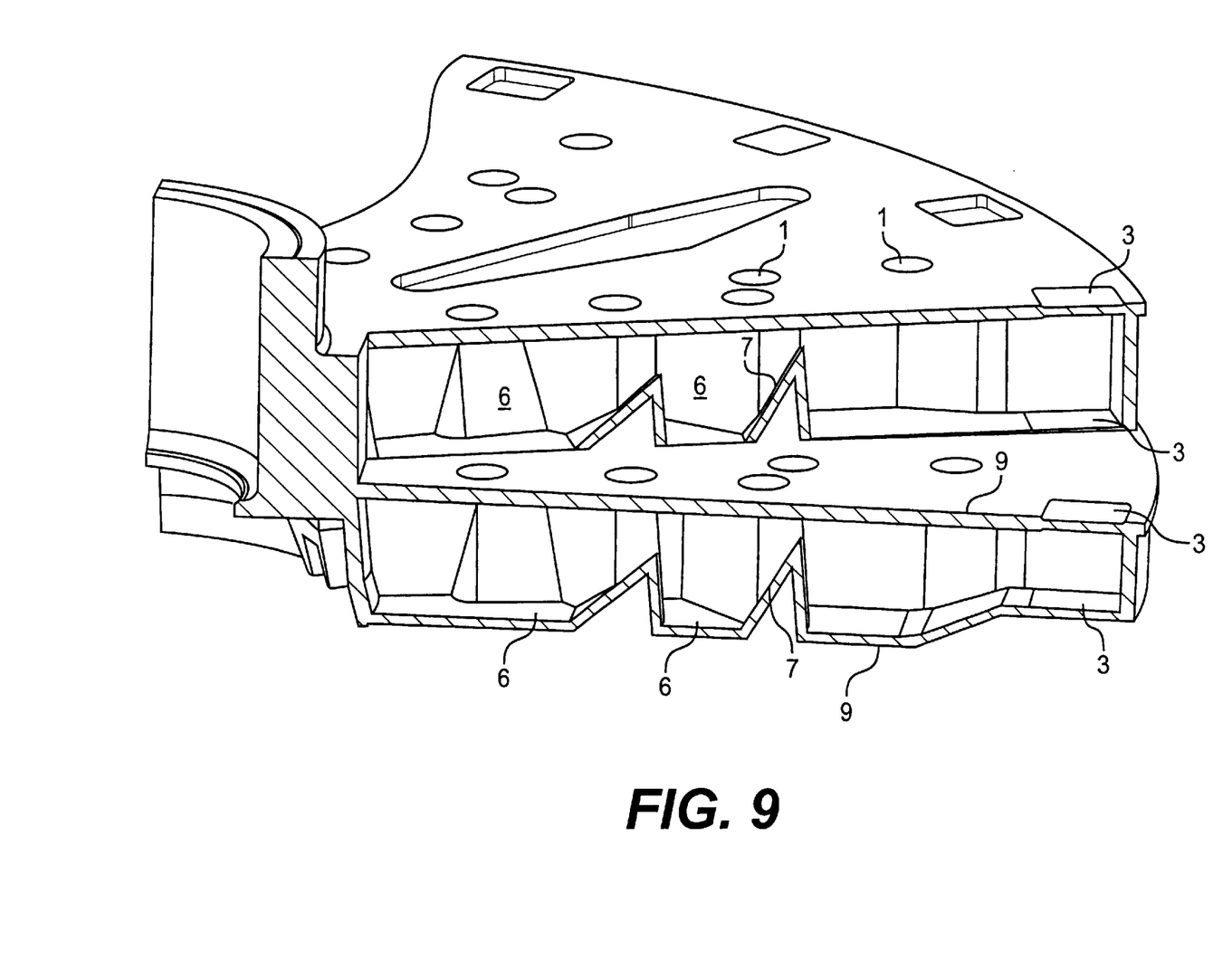
FIG. 9 is a cross-sectional view of a portion of a multi-cell rotor according to the present invention and including chambers arranged above one another and offset in relation to one another.
Figure 10:
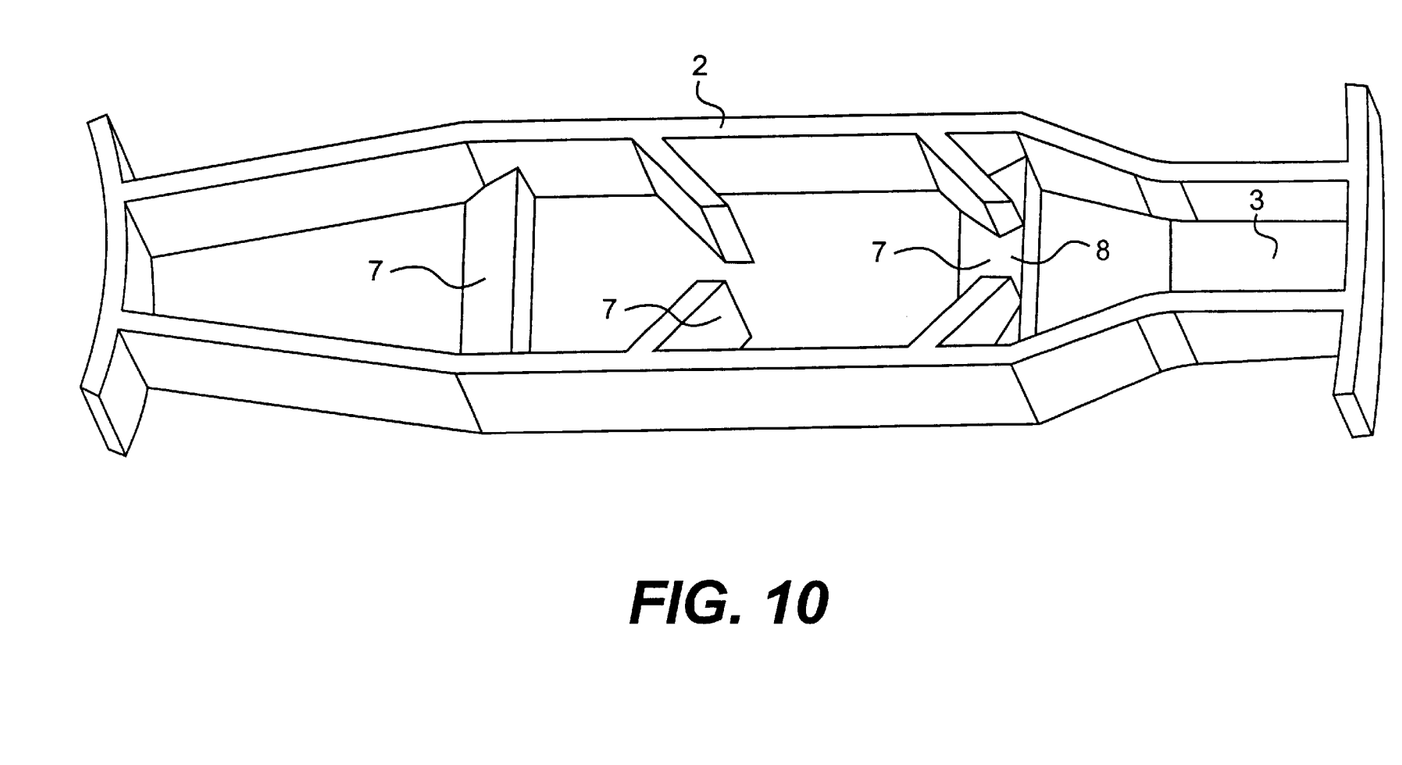
FIG. 10 is a top sectional view of a cell having a special design with ramps 7 on both sides, by means of which nozzles 8 can be formed in combination with horizontal ramps.

A particularly efficient utilization of the surface available on the rotor is illustrated according to the embodiments shown in FIGS. 7 and 8, in which several chambers which are filled with different reagents can be arranged above one another. As shown in FIGS. 7 and 8, the measurement cells are fed from a plurality of chambers or chamber combinations lying adjacent to one another or lying above one another in a plurality of layers or are fed in parallel. The measurement windows of said measurement cells can be offset tangentially or radially or in the direction of the axis of rotation in relation to the measurement windows of other measurement cells. A high degree of design flexibility, by which means a very wide variety of analytical conditions can be satisfied, is shown in FIG. 9 in which the chambers arranged above one another can also be offset tangentially or radially in relation to one another. The chambers can be provided with one or more pipette holes and can be divided from one another by ramps. The special construction, shown in FIG. 10, of a chamber equipped with ramps 7 and nozzles 8 guarantees particularly intensive mixing of the reagents and the fluid to be examined.

Figure 11:
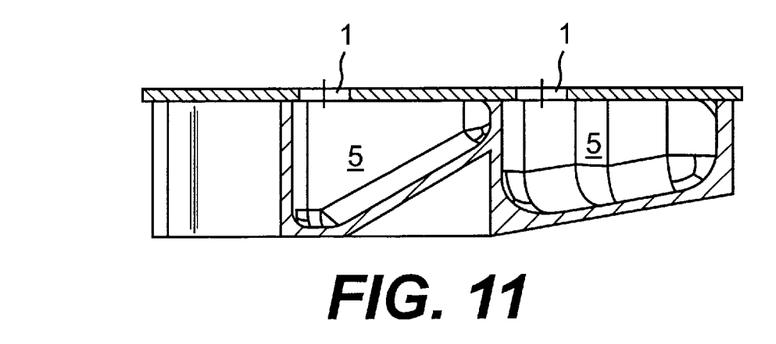
FIG. 11 is a cross-sectional view of a cell having chambers with rounded wall transitions.
Figure 12:
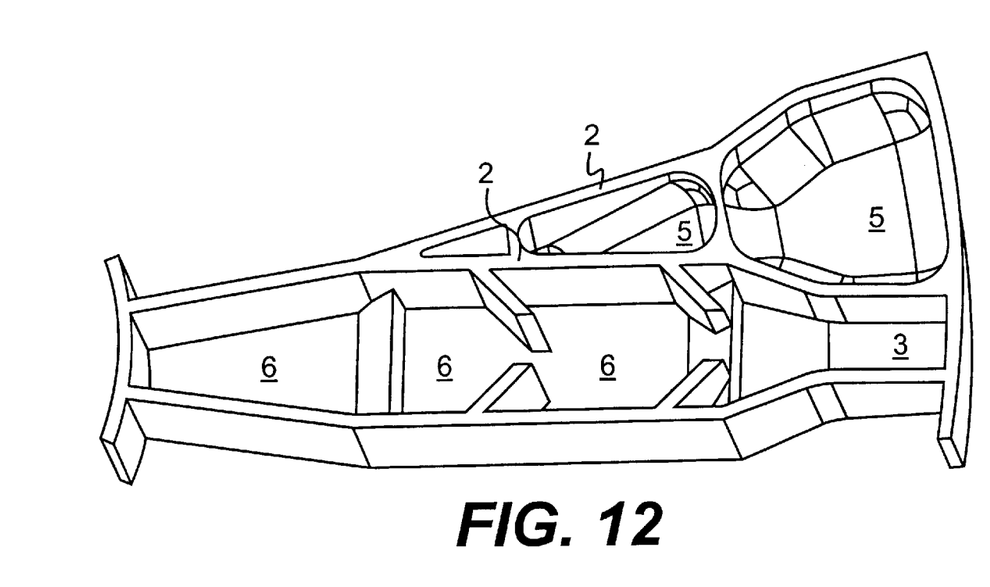
FIG. 12 is a top sectional view of the cell of FIG. 11 having chambers with rounded wall transitions.

A chamber construction making optimum use of the reagents present is embodied in FIGS. 11 and 12. By means of rounding all the corners of the chambers, it is possible to prevent the otherwise unavoidable loss of reagent quantities remaining in the chamber corners, especially in the case of preliminary dilutions and preliminary reactions.

Figure 13:
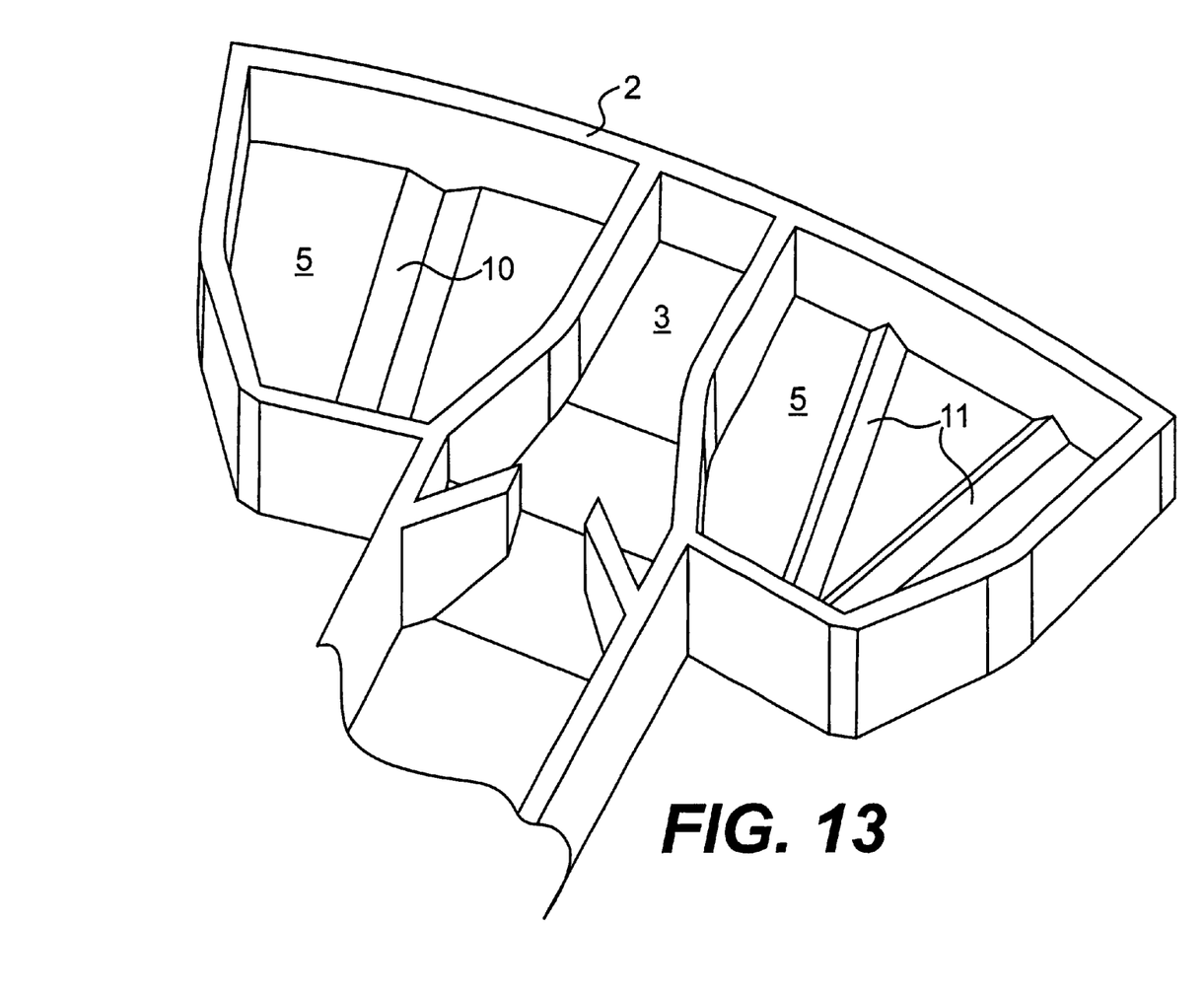
FIG. 13 is a top sectional view of chambers including a groove or rib structure on the base of the chamber.

The versatility of the multi-cell rotor according to the invention can be still further improved by means of further refinements. For example, it is possible to form the measurement windows as optical lenses, making especially precise measurements possible. A further improvement is embodied and shown in FIG. 13, wherein the chamber bases 9 have a groove 10 or rib structure 11 which produces a capillary action and thereby permits all of the reagent solution to flow off in the direction under the pipette hole. In the multi-cell rotor according to the present invention, chambers are also expediently provided for specific purposes, e.g. whole-blood chambers 4 for breaking whole blood up into plasma and blood cells, which chambers can be equipped with measurement windows 3 and from which the plasma can be again removed. In addition, chambers for preliminary dilutions and/or preliminary reactions 5 and chambers for separation of fluids can also be provided.

The multi-cell rotor itself is generally made of a single transparent thermoplastic material such as polystyrene (PS), polycarbonates or polymethyl methacrylate (PMMA). However, its individual parts can also be made of different thermoplastic materials. It is particularly advantageous, however, for the multi-cell rotor to be produced using a multi-component material. The reagents, some of which are very sensitive, then remain protected from the effects of light in the largely opaque entry chambers 6.

List of reference numbers:

1 Pipette hole
2 Ridges
3 Measurement window
4 Whole-blood chamber
5 Preliminary dilution chamber
6 Entry chamber
7 Ramp
8 Nozzle
9 Base
10 Grooves with capillary action
11 Ribs with capillary action

What is claimed is:

1. A multi-cell rotor for an automatic analyzer for examining biological fluids, comprising:
a rotor base surface; and
a plurality of cells arranged on the rotor base surface such that substantially the entire rotor base surface is covered by the plurality of cells, wherein each cell has two side walls and includes a measurement cell and at least two chambers, the measurement cell being in fluid communication with the at least two chambers, and wherein at least a first one of the plurality of cells has a first end positioned at an inner edge of the rotor base surface, a second end located at an outer edge of the rotor surface, and a first shape substantially defined by the side walls and wherein at least a second one of the plurality of cells has a first end located approximately midway between the inner edge of the rotor base surface and the outer edge of the rotor base surface, a second end located at the outer edge of the rotor base surface, and a second shape substantially defined by the side walls and different from the first shape.

2. The multi-cell rotor as claimed in claim 1, wherein the measurement cells have radially arranged optical measurement windows situated at identical radial distances from one another.

3. The multi-cell rotor as claimed in claim 1, wherein the measurement cells have radially arranged optical measurement windows situated at different radial distances from one another.

4. The multi-cell rotor as claimed in claim 1, wherein the measurement cells have radially arranged measurement windows located at nonuniform tangential distances from the axis of rotation of the rotor.

5. The multi-cell rotor as claimed in claim 1, wherein measurement windows of the measurement cells are identically sized.

6. The multi-cell rotor as claimed in claim 1, wherein measurement windows of the measurement cells are differently sized.

7. The multi-cell rotor as claimed in claim 1, wherein measurement windows of the measurement cells are optical lenses.

8. The multi-cell rotor as claimed in claim 1, wherein measurement windows of the measurement cells lie at different distances from one another in an axial direction.

9. The multi-cell rotor as claimed in claim 1, wherein the measurement cell is fed in parallel or from a plurality of chambers or chamber combinations lying adjacent to one another or lying above one another in a plurality of layers, wherein measurement windows of said measurement cell can be offset tangentially, radially, or in the direction of the axis of rotation in relation to the measurement windows of other measurement cells.

10. The multi-cell rotor as claimed in claim 1, wherein each chamber is provided with at least one pipette hole, and wherein the chambers can be divided from one another by horizontal ramps.

11. The multi-cell rotor as claimed in claim 1, wherein the chambers have vertical ramps on one or both sides of the chamber, by which nozzles are formed in combination with horizontal ramps.

12. The multi-cell rotor as claimed in claim 1, wherein the chambers have rounded wall transitions.

13. The multi-cell rotor as claimed in claim 1, wherein the chambers include bases having a groove or rib structure with capillary action.

14. The multi-cell rotor as claimed in claim 1, further comprising whole-blood chambers, chambers for preliminary dilutions and/or preliminary reactions, and chambers for separation of fluids.

15. The multi-cell rotor as claimed in claim 1, wherein said rotor contains chambers for breaking whole blood up into plasma and blood cells, said chambers equipped with measurement windows, and wherein the plasma can be removed from the chambers via said measurement windows.

16. The multi-cell rotor as claimed in claim 15, wherein the chambers communicate with additional chambers so that reagent can be added and admixed.

17. The multi-cell rotor as claimed in claim 1, wherein said rotor is made of one of group consisting of a single transparent thermoplastic material, individual parts made of different thermoplastic materials, and a multi-component material.

18. The multi-cell rotor of claim 1, wherein the first shape is substantially rectangular and the second shape is substantially triangular.

19. The multi-cell rotor of claim 1, wherein the side walls defining the first shape are substantially parallel.

20. The multi-cell rotor of claim 1, wherein the side walls defining the second shape intersect one another.

21. A multi-cell rotor for an automatic analyzer for examining biological fluids, comprising measurement cells of different configurations and chambers of different geometries, in identical or different configurations, arranged on said rotor, wherein the cells and chambers receive different volumes of fluid, are used for preparing for measurements, and are in fluid communication with one another, wherein measurement windows of the cells lie at different distances from one another in an axial direction.

22. A multi-cell rotor for an automatic analyzer for examining biological fluids, comprising measurement cells of different configurations and chambers of different geometries, in identical or different configurations, arranged on said rotor, wherein the cells and chambers receive different volumes of fluid, are used for preparing for measurements, and are in fluid communication with one another, wherein the chambers have vertical ramps on one or both sides of the chamber, by which nozzles are formed in combination with horizontal ramps.

23. A multi-cell rotor for an automatic analyzer for examining biological fluids, comprising measurement cells of different configurations and chambers of different geometries, in identical or different configurations, arranged on said rotor, wherein the cells and chambers receive different volumes of fluid, are used for preparing for measurements, and are in fluid communication with one another, wherein the chambers include bases having a groove or rib structure with capillary action.

24. A multi-cell rotor for an automatic analyzer for examining biological fluids, comprising:

a base surface; and a plurality of substantially longitudinal walls extending upward from the base surface to form a plurality of cells, wherein each of the plurality of walls forms a side wall for two different cells, and wherein each cell includes a measurement cell and at least two chambers, the measurement cell being in fluid communication with the at least two chambers.

25. The multi-cell rotor of claim 24, wherein at least a first one of the plurality of cells has a first shape substantially defined by the side walls and wherein at least a second one of the plurality of cells has a second shape substantially defined by the side walls and different from the first shape.

26. The multi-cell rotor of claim 25, wherein the first shape is substantially rectangular and the second shape is substantially triangular.

27. The multi-cell rotor of claim 25, wherein the side walls defining the first shape are substantially parallel.

28. The multi-cell rotor of claim 25, wherein the side walls defining the second shape intersect one another.

29. A multi-cell rotor for an automatic analyzer for examining biological fluids, comprising:

a plurality of cells arranged on a rotor, each cell having two side walls, wherein each side wall functions as a side wall for two adjacent cells, and each cell further including a measurement cell and at least two chambers, the measurement cell being in fluid communication with the at least two chambers.

30. The multi-cell rotor of claim 29, wherein at least a first one of the plurality of cells has a first shape substantially defined by the side walls and wherein at least a second one of the plurality of cells has a second shape substantially defined by the side walls and different from the first shape.

31. The multi-cell rotor of claim 29, further comprising a rotor base surface, wherein the plurality of cells are arranged on the rotor base surface such that substantially the entire rotor base surface is covered by the plurality of cells.

32. The multi-cell rotor of claim 29, wherein at least a first one of the plurality of cells has a first end positioned at an inner edge of the rotor and a second end located at an outer edge of the rotor surface, and wherein at least a second one of the plurality of cells has a first end located approximately midway between the inner edge of the rotor base surface and the outer edge of the rotor base surface, a second end located at the outer edge of the rotor base surface.

33. The multi-cell rotor of claim 32, wherein the first one of the plurality of cells has a first shape substantially defined by the side walls and wherein the second one of the plurality of cells has a second shape substantially defined by the side walls and different from the first shape.

* * * * *